United States Patent
Howard

(10) Patent No.: US 11,096,653 B2
(45) Date of Patent: Aug. 24, 2021

(54) NETWORKED ELECTRONIC STETHOSCOPE

(71) Applicant: Newton Howard, Providence, RI (US)

(72) Inventor: Newton Howard, Providence, RI (US)

( * ) Notice: Subject to any disclaimer, the term of this patent is extended or adjusted under 35 U.S.C. 154(b) by 23 days.

(21) Appl. No.: 15/431,221

(22) Filed: Feb. 13, 2017

(65) Prior Publication Data

US 2017/0231597 A1   Aug. 17, 2017

Related U.S. Application Data

(60) Provisional application No. 62/294,421, filed on Feb. 12, 2016.

(51) Int. Cl.
| | |
|---|---|
| *A61B 7/04* | (2006.01) |
| *A61B 5/00* | (2006.01) |
| *G16H 40/67* | (2018.01) |
| *A61B 5/25* | (2021.01) |
| *A61B 5/332* | (2021.01) |

(52) U.S. Cl.
CPC ............. *A61B 7/04* (2013.01); *A61B 5/0022* (2013.01); *A61B 5/0024* (2013.01); *A61B 5/25* (2021.01); *A61B 5/332* (2021.01); *G16H 40/67* (2018.01)

(58) Field of Classification Search
CPC ........................................................ A61B 7/04
See application file for complete search history.

(56) References Cited

U.S. PATENT DOCUMENTS

| | | | | |
|---|---|---|---|---|
| 4,362,164 A | * | 12/1982 | Little .................. | A61B 5/0404 600/382 |
| 7,346,174 B1 | * | 3/2008 | Smith .................... | A61B 7/026 381/67 |
| 2002/0111777 A1 | * | 8/2002 | David ................ | A61B 5/04085 702/189 |
| 2004/0220487 A1 | * | 11/2004 | Vyshedskiy .......... | A61B 5/0002 600/513 |

(Continued)

OTHER PUBLICATIONS

Datasheet for Burr-Brown INA116 Ultra Low Input Bias Current Instrumentation Amplifier, Burr-Brown Corporation, May 1995.

(Continued)

*Primary Examiner* — Rex R Holmes
*Assistant Examiner* — Jennifer L Ghand
(74) *Attorney, Agent, or Firm* — Smith, Gambrell & Russell, LLP

(57) ABSTRACT

Embodiments of the present systems and methods may provide improved electronic stethoscopes that provide diversified diagnosis functionality. For example, embodiments may provide the capability to diagnose a wide range of pathologies by using the device's wireless network capacity to link it to wearable sensors of different kinds, maintaining the traditional use of the stethoscope while enabling it to sense a whole new set of physiological signals. For example, in an embodiment, a system may comprise a networked electronic stethoscope and a sensor adapted to be attached to the networked electronic stethoscope, the sensor comprising an electrode adapted to obtain a signal representing a physiological parameter of a patient, a processor adapted to digitize and process the obtained signal to form data, and a wireless network adapter adapted to transmit the data to the networked electronic stethoscope.

12 Claims, 12 Drawing Sheets

(56) References Cited

U.S. PATENT DOCUMENTS

| | | | | |
|---|---|---|---|---|
| 2008/0232604 A1* | 9/2008 | Dufresne | ............... | A61B 5/061 |
| | | | | 381/67 |
| 2011/0190665 A1* | 8/2011 | Bedingham | .............. | A61B 7/04 |
| | | | | 600/586 |
| 2013/0116584 A1* | 5/2013 | Kapoor | .................... | A61B 5/02 |
| | | | | 600/513 |
| 2014/0364755 A1* | 12/2014 | Sankai | .................... | A61B 5/332 |
| | | | | 600/513 |
| 2015/0164340 A1* | 6/2015 | Bedingham | .............. | A61B 7/04 |
| | | | | 600/484 |
| 2016/0262717 A1* | 9/2016 | Smith | .................. | A61B 5/0022 |
| 2017/0185737 A1* | 6/2017 | Kovacs | .................... | A61B 7/04 |
| 2018/0028144 A1* | 2/2018 | Chen | .................... | A61B 5/0245 |
| 2018/0085062 A1* | 3/2018 | Lee | ...................... | A61B 5/7278 |

OTHER PUBLICATIONS

Y. M. Chi and G. Cauwenberghs, "Wireless Non-contact EEG/ECG Electrodes for Body Sensor Networks," 2010 International Conference on Body Sensor Networks, Singapore, 2010, pp. 297-301, doi: 10.1109/BSN.2010.52.

3M™ Littmann® Electronic Stethoscopes, Model 3200, 3M Health Care, 2012.

\* cited by examiner

900

NETWORKED ELECTRONIC STETHOSCOPE

CROSS-REFERENCE TO RELATED APPLICATIONS

This application claims the benefit of U.S. Provisional Application No. 62/294,421, filed Feb. 12, 2016, the contents of which are incorporated herein in their entirety.

BACKGROUND

The present invention relates to techniques for expanding the functionality of a traditional stethoscope, enabling it to digitally measure and store several physiological signals and transform the common stethoscope into a diversified diagnostic tool which would be useful across a wide spectrum of medical fields.

Conventional mechanical acoustic stethoscopes may be used to listen to the internal sounds of a body and have been in common use by physicians for many years. More recently, electronic stethoscopes have provided improved functionality over mechanical stethoscopes. A typical electronic stethoscope may include a built-in microphone, connected to a micro controller and a network interface, such as a Bluetooth chip, enabling it to record sounds during patient examination and digitally store the recording in a linked computer through wireless network, such as Bluetooth, communication. Such a stethoscope may possess a built-in controller with a digital screen that can be used to trigger several actions and can be expanded by developers with the help of dedicated APIs.

However, the conventional electronic stethoscopes still provide relatively limited information, and do not provide diversified diagnosis functionality. Typically, the use of the conventional stethoscope in medicine, while not insignificant, has been limited to pulmonary applications and has not been adapted to diagnose a wider range of pathologies.

Accordingly, a need arises for improved electronic stethoscopes that provide diversified diagnosis functionality.

SUMMARY

Embodiments of the present systems and methods may provide improved electronic stethoscopes that provide diversified diagnosis functionality. For example, embodiments may provide the capability to diagnose a wide range of pathologies by using the device's wireless network capacity to link it to wearable sensors of different kinds, maintaining the traditional use of the stethoscope while enabling it to sense a whole new set of physiological signals For example, in an embodiment, a system may comprise a networked electronic stethoscope and a sensor adapted to be attached to the networked electronic stethoscope, the sensor comprising an electrode adapted to obtain a signal representing a physiological parameter of a patient, a processor adapted to digitize and process the obtained signal to form data, and a wireless network adapter adapted to transmit the data to the networked electronic stethoscope.

In an embodiment, the electrode may be a non-contact electrode adapted to obtain a signal representing a physiological parameter of the patient without direct contact with the patient. The system may further comprise at least one additional sensor comprising an electrode adapted to obtain a signal representing a physiological parameter of the patient. The at least one additional sensor may be communicatively connected to the sensor adapted to be attached to the networked electronic stethoscope. The at least one additional sensor may be communicatively connected to the sensor adapted to be attached to the networked electronic stethoscope via at least one wire. The at least one additional sensor may be communicatively connected to the sensor adapted to be attached to the networked electronic stethoscope via a wireless communication network. The sensor may be adapted to be attached to a membrane support circle the networked electronic stethoscope. The system may further comprise at least one additional sensor comprising an electrode adapted to obtain a signal representing a physiological parameter of the patient. The processor may be adapted to generate a representation of the physiological parameter of the patient based on at least the signal representing the physiological parameter of a patient obtained from the sensor adapted to be attached to the networked electronic stethoscope and the signal representing the physiological parameter of a patient obtained from the at least one additional sensor. The processor may be adapted to generate a plurality of representations of the physiological parameter of the patient based on at least a plurality of signals representing the physiological parameter of a patient obtained from the sensor adapted to be attached to the networked electronic stethoscope, placed at each of a plurality of locations on the patient, and the signal representing a physiological parameter of a patient obtained from the at least one additional sensor. The signal representing the physiological parameter of the patient may be an electrocardiogram (EKG) signal.

For example, in an embodiment, a method may comprise placing at a location on a patient at least one sensor comprising an electrode adapted to obtain a signal representing a physiological parameter of the patient, repeatedly placing at a different location on the patient a sensor attached to a networked electronic stethoscope, the networked electronic stethoscope comprising an electrode adapted to obtain a signal representing a physiological parameter of a patient, a processor adapted to digitize and process the obtained signal to form data, and a wireless network adapter adapted to transmit the data to the networked electronic stethoscope, and for each different location on the patient at which the sensor is placed, obtaining the signal representing the physiological parameter of the patient.

In an embodiment, the electrodes may be non-contact electrodes adapted to obtain a signal representing a physiological parameter of the patient without direct contact with the patient. The at least one sensor may be communicatively connected to the sensor attached to the networked electronic stethoscope. The at least one sensor may be communicatively connected to the sensor attached to the networked electronic stethoscope via at least one wire. The at least one sensor is communicatively connected to the sensor attached to the networked electronic stethoscope via a wireless communication network. The signal representing the physiological parameter of the patient is an electro-cardiogram (EKG) signal.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Figure 1:
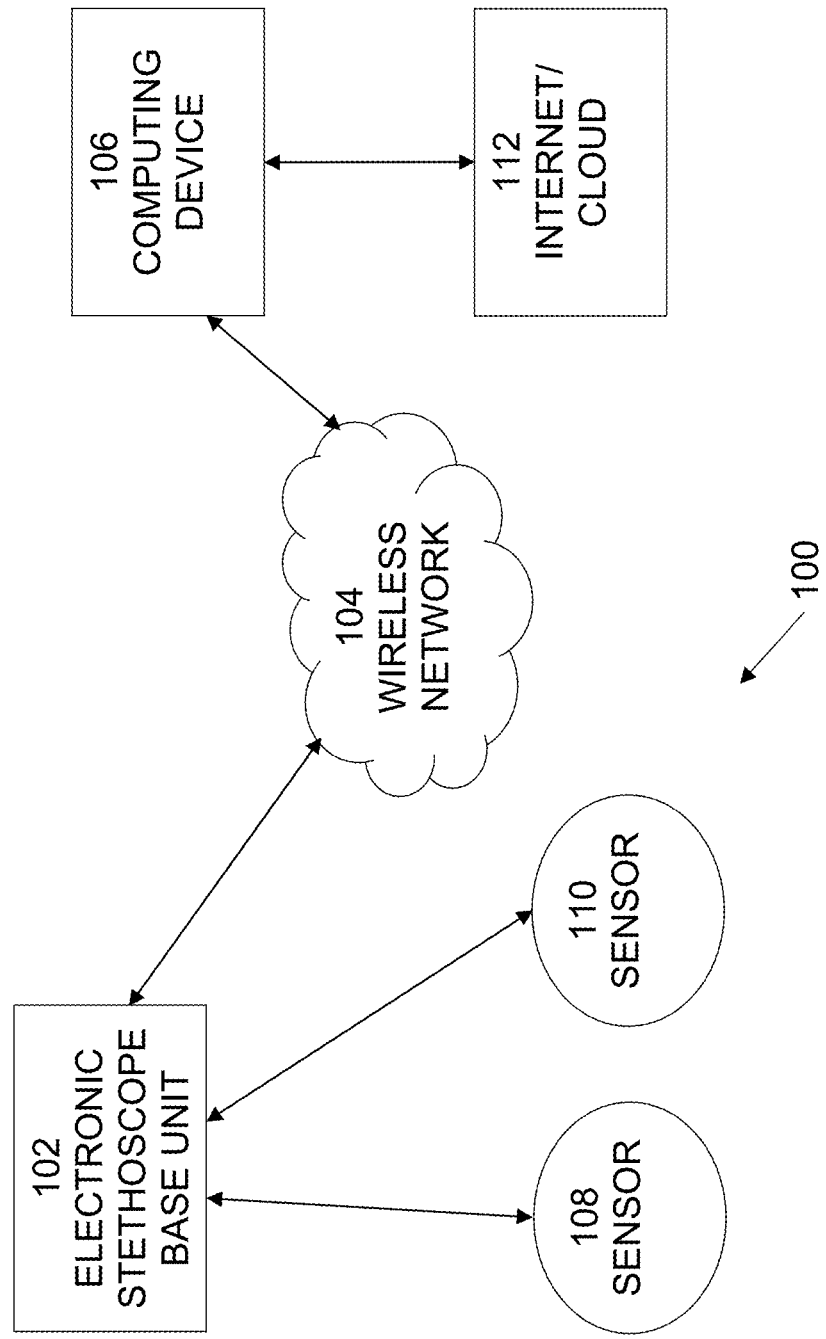
FIG. 1 is an exemplary block diagram of a communication network, in which embodiments of the present systems and methods may be implemented.

Embodiments of the present systems and methods may provide improved electronic stethoscopes that provide diversified diagnosis functionality. For example, embodiments may provide the capability to diagnose a wide range of pathologies by using the device's wireless network capacity to link it to wearable sensors of different kinds, maintaining the traditional use of the stethoscope while enabling it to sense a whole new set of physiological signals An exemplary block diagram of a communication network 100, in which embodiments of the present systems and methods may be implemented, is shown in FIG. 1. Network 100 may include electronic stethoscope/base unit 102, wireless network 104, computing device 106, and sensors 108, 110, and computing device 106 may be connected to the Internet and/or cloud facilities 112. Electronic stethoscope/base unit 102 may include functionality of a conventional stethoscope, but also may provide the capability to record signals from sensors 108, 110 and digitally store the recordings in a linked computing device 106 through wireless network 104. Such a system may provide the capability for a patient can get their recordings, and submit them to other practitioners for second opinion without need of any redundant examination. Further, doctors can analyze the recordings later in a non-clinical setting, can replay the recordings, and can even apply different layers of filtration and signal processing algorithms on the recording. Further, patient data may be uploaded to the cloud 112 to be applied against volumes of prior patient data for research purposes or even automated diagnostic assistance.

Wireless network 104 may include any type of wireless communication network that may be used to communicate information. Computing device 106 may be any type or number of computers or data processing systems, including, but not limited to personal computers, servers, special purpose data processors, etc. Sensors 108, 110 may include any type of sensor that may be used to obtain information about physical parameters of signals of a living organism. Examples of such sensors may include, but are not limited to, acoustic sensors, pressure sensors, optical sensors, temperature sensors, electrical sensors, etc. Sensors 108, 110 may be communicatively connected to electronic stethoscope/base unit 102. Such communicative connections may use wired or wireless connections. In addition, sensors 108, 110 may be physically or electrically connected to electronic stethoscope/base unit 102, or sensors 108, 110 may be physically or electrically remote from, or isolated from, electronic stethoscope/base unit 102.

For example, electronic stethoscope/base unit 102 may include wireless network, such as Bluetooth, capability, which may be used to link electronic stethoscope/base unit 102 with sensors 108, 110 of different kinds, such as wearable sensors. For example, electronic stethoscope/base unit 102 may provide EKG acquisition functionality. This may be done without overcomplicating data acquisition and minimally disrupting existing clinical processes. Important elements within an EKG machine are its electrode sets. Accordingly, wireless electrodes in combination with a wireless network stethoscope, may provide advantageous functionality.

Figure 2:
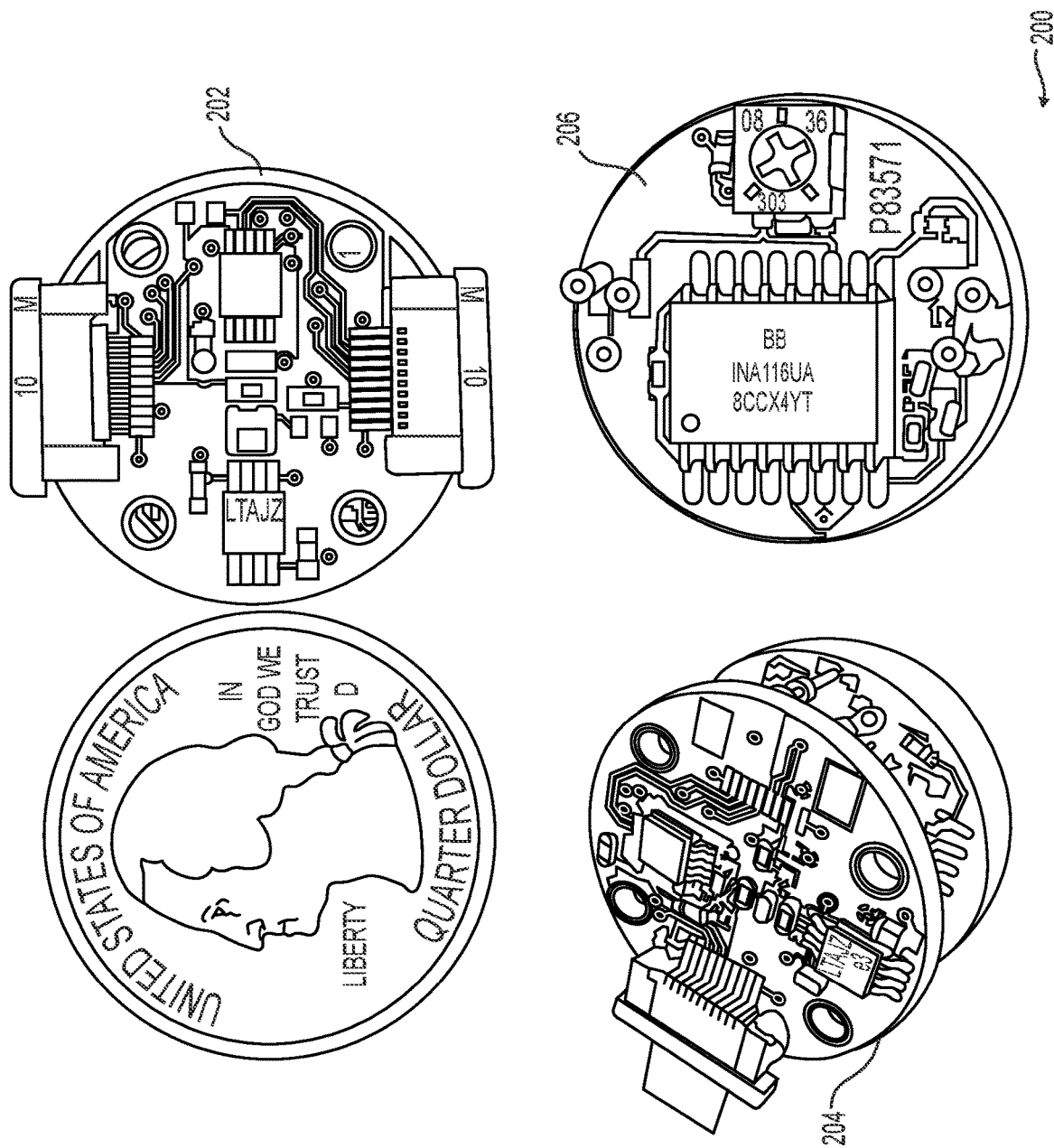
FIG. 2 is an exemplary diagram of exemplary embodiment of a sensor, such as a non-contact electrode device.

Sensors 108, 110 may include a set of capacitive electrodes manufactured on a printed circuit board that is able to operate through fabric or other insulation. An exemplary embodiment of a sensor, such as a non-contact electrode device 200 is shown in FIG. 2. The upper PCB 202 may include a differential amplifier and ADC along with two serial daisy chain connectors. A side view of the electrode 204 shows the upper PCB 202 and lower PCB 206 joined together. The lower PCB 206 may include and ultra-high input impedance amplifier front-end. The bottom of this PCB may be a solid, insulated copper fill, which may function as a capacitive electrode.

In an exemplary embodiment, an electrode device 200 may provide 46 dB of gain over a 0.7-100 Hz bandwidth with a noise level of 3.8 µV RMS for high quality brain and cardiac recordings. Signals may be digitized directly in the device 200 and are may be transmitted over a wired or wireless connection. For example, a wired connection may include a digital serial daisy chain connecting all of the electrodes, which would minimize the number of wires required on the body. Referring briefly to FIG. 1, a small wireless base unit 102 may transmit EEG/EKG telemetry to a computing device 106 for storage and processing.

Figure 3:
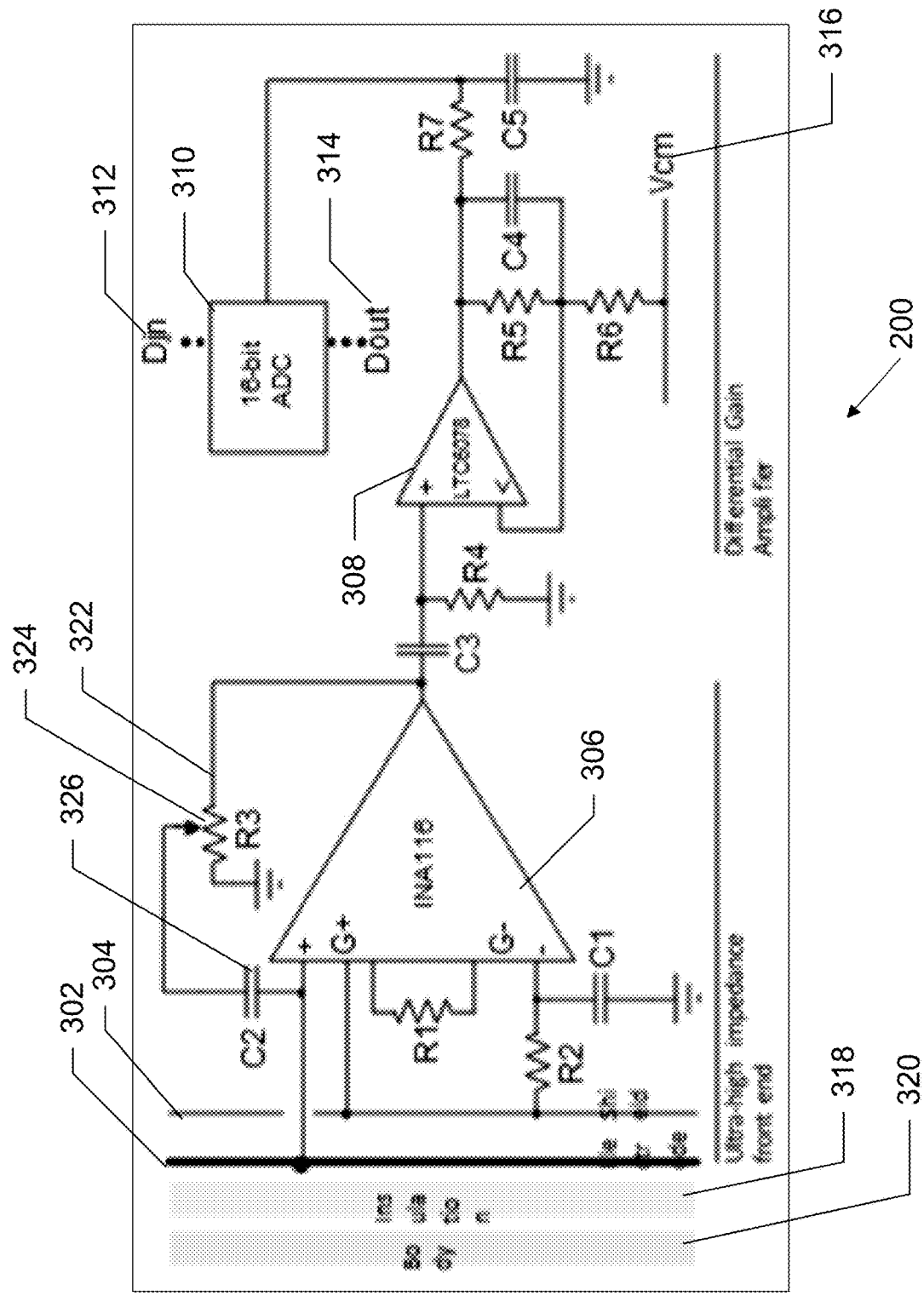
FIG. 3 is an exemplary schematic diagram of an embodiment of a wireless non-contact electrode sensor.

The system may include a set of non-contact bio-potential sensors 200 which may be connected along a single common wire. An exemplary schematic diagram of a wireless non-contact electrode sensor 200 is shown in FIG. 3. The sensors 200 may either be in direct contact with the skin or embedded within fabric and clothing. Sensors 200 may include an electrode 302 to detect the desired signal, a single adhesive or dry contact sensor (not shown) that may be placed anywhere convenient is used to establish the ground reference for the system. As shown in FIG. 3, a sensor 200 may include and ultra-high input impedance front-end amplifier 306, such as an INA116, a differential amplifier 308, such as an LTC6078, and an analog-to-digital converter (ADC) 310, such as a 16-bit ADC. The voltages at nodes Din 312, Dout 312, and Vcm 312 may be carried along the daisy chain. Each electrode may be constructed from two PCBs, each, for example, the size of a US quarter, stacked upon one another. The upper PCB contains a low noise differential amplifier and a 16-bit ADC. Rather than outputting a single analog signal, the electrode may output a digitized value, which can be carried in a serial daisy chain to drastically reduce the number of wires needed. A miniature ribbon cable may carry the power supply, digital control as well as analog common mode reference from electrode-to-electrode.

The lower PCB contains the INA116, configured as an ultra-high input impedance amplifier. The bottom surface of the PCB is a solid copper fill, insulated by a solder mask, which functions as the electrode. This surface forms a coupling capacitor with the body. An active shield formed in a solid inner plane protects the electrode from external noise pick-up. To minimize the shield capacitance, an extra thick PCB is used for the electrode. The full schematic of the two PCBs of the non-contact electrode is shown in FIG. 2, above.

Designing an ultra-high input impedance amplifier with low noise levels is the main challenge in implementing non-contact electrodes. A simplified, generic model for a capacitive sensor that is directly applicable to the circuit used in this design is shown in FIG. 3. The sensor may include electrode 302 to detect the desired signal, an electrical shield 304, and insulation 318 to prevent direct electrical contact with the body 320 of the subject being monitored. Signal sources from the body (EEG/EKG) may be thought of as a voltage source, Vs, connected to the input of an amplifier via a small coupling capacitance, Cs. All real amplifiers will also have some finite resistance, Rb, and input capacitance. A small amount of positive feedback 322 may be applied through C2 324, as adjusted using R3 326, to neutralize the effect of the input capacitance for better channel matching and common-mode rejection ratio (CMRR).

Important noise sources may include the input-referred voltage noise of the amplifier, $V_{na}$, the input current noise, $I_{na}$ and the additional current noise, $I_{nb}$, due to the leakage and conductance of the biasing element. The current noise contribution may be either 4kTR thermal noise for a resistive device or 2qI shot noise for a PN junction. Bootstrapping may be used to electronically boost the effective impedance of the biasing element, but the noise contribution may depend only on the physical resistance or leakage current, illustrating the challenge in finding suitable components for a non-contact sensor. The total input referred noise of a capacitive amplifier may be written as, $$v_n^2 = v_{na}^2 \left(1 + \frac{C_{in} + C_n}{C_S}\right)^2 + \frac{i_{na}^2 + i_{nb}^2}{\omega^2 C_S^2}.$$

This equation shows the effect of the parasitic input capacitances and leakage currents on the noise performance of the amplifier and the difficulty in designing a non-contact electrode. Any excess input capacitance may directly multiply the effect of the amplifier's input voltage noise as $C_m+C_n>C_s$. Furthermore, since biopotential signals are at low frequencies (0.1-100 Hz), even small amounts of current noise may become integrated into large amounts of input voltage noise. This necessitates an amplifier with very low input and guard capacitance, as well as almost zero leakage currents.

The INA116, originally by Burr-Brown, now produced by Texas Instruments, is an example of an amplifier that is well known for ultra-high input impedance applications by virtue of its extremely low current noise (0.1 fA/Hz). However, any other comparable amplifier may be used for this application. Any circuit introduced to bias the inputs may significantly degrade the noise performance of the amplifier. An extremely difficult to obtain resistor (greater than 1 TΩ) would be required to match the current noise specification of the INA116. The INA116 may reliably charge a floating input to a point inside the allowable input range shortly after power-up, purely through leakage currents, removing the need for any external bias network. To remove drift and DC offsets, a low-passed version of the input signal was taken from the non-inverting input's guard and connected to the inverting input. This effectively performs AC coupling without degrading the input impedance and centers the output to mid-rail for maximum signal swing. The overall gain of the first stage INA116 may be written as $$A_v = \left(1 + \frac{50k\Omega}{R_1}\right) \times \frac{sR_2C_1}{1+sR_2C_1}.$$

For this exemplary application the cut-off frequency may be set at 0.7 Hz and the amplifier may be configured with a gain of 2.02. This relatively low gain value was dictated by the limited voltage headroom of the INA116, which was operated with only a 5V power supply, not the datasheet recommended 10V.

Electrocardiography (EKG or EKG) is the process of recording the electrical activity of the heart over a period of time using electrodes placed on a patient's body. These electrodes detect the tiny electrical changes on the skin that arise from the heart muscle depolarizing during each heartbeat.

In a conventional 12 lead EKG, ten electrodes are placed on the patient's limbs and on the surface of the chest. The overall magnitude of the heart's electrical potential is then measured from twelve different angles ("leads") and is recorded over a period of time (usually 10 seconds). In this way, the overall magnitude and direction of the heart's electrical depolarization is captured at each moment throughout the cardiac cycle. The graph of voltage versus time produced by this non-invasive medical procedure is referred to as an electrocardiogram.

In an embodiment, an electronic stethoscope may be enabled with this 12 lead EKG diagnostic capability, which may provide the most precise output existing in clinical use. An EKG acquisition comes from a set of electrodes applied to a patient's body, or with non-contact electrodes, on some fabric or clothing. The locations of the electrodes on a patient are as follows:

Electrode Name Electrode Placement

RA On the right arm, avoiding thick muscle.

LA In the same location where RA was placed, but on the left arm.

RL On the right leg, lateral calf muscle.

LL In the same location where RL was placed, but on the left leg.

$V_1$ In the fourth intercostal space (between ribs 4 and 5) just to the right of the sternum (breastbone).

$V_2$ In the fourth intercostal space (between ribs 4 and 5) just to the left of the sternum.

$V_3$ Between leads $V_2$ and $V_4$.

$V_4$ In the fifth intercostal space (between ribs 5 and 6) in the mid-clavicular line.

$V_5$ Horizontally even with $V_4$, in the left anterior axillary line.

$V_6$ Horizontally even with $V_4$ and $V_5$ in the midaxillary line.

The signals obtained from each of these electrodes may then be combined in 12 different ways to build the EKG's 12 leads. These 12 leads are divided between the Limb Leads, Augmented Limb Leads, and Precordial Leads. First is the definition of the Wilson's central terminal, which is commonly used in the definition of many of the leads.

$$V_W = \frac{1}{3}(RA + LA + LL).$$

Figure 4:
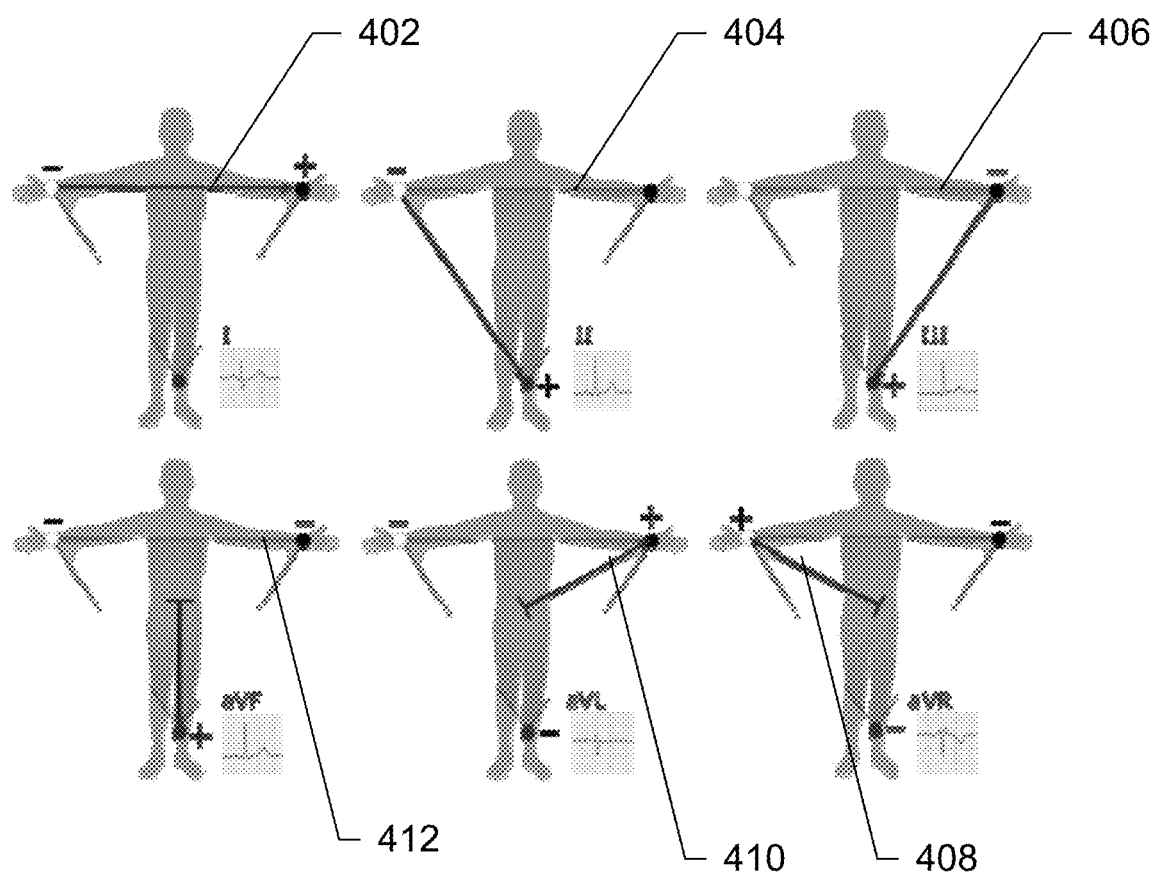
FIG. 4 is an exemplary diagram of voltage differences making up the Limb Leads and Augmented Limb Leads.

The voltage differences making up the Limb Leads and Augmented Limb Leads are shown in FIG. 4. Leads I, II and III are called the Limb Leads. The electrodes that form these signals are located on the limbs—one on each arm and one on the left leg.

Lead I 402 is the voltage between the (positive) left arm (LA) electrode and right arm (RA) electrode:

$$I = LA - RA$$

Lead II 404 is the voltage between the (positive) left leg (LL) electrode and the right arm (RA) electrode:

$$II = LL - RA$$

Lead III 406 is the voltage between the (positive) left leg (LL) electrode and the left arm (LA) electrode:

$$III = LL - LA$$

Leads aVR, aVL, and aVF are the Augmented Limb Leads. They are derived from the same three electrodes as leads I, II, and III, but they use Wilson's central terminal as their negative pole.

Lead augmented Vector Right (aVR) 408 has the positive electrode on the right arm. The negative pole is a combination of the left arm electrode and the left leg electrode:

$$aVR = RA - \frac{1}{2}(LA + LL) = \frac{3}{2}(RA - V_W)$$

Lead augmented Vector Left (aVL) 410 has the positive electrode on the left arm. The negative pole is a combination of the right arm electrode and the left leg electrode:

$$aVL = LA - \frac{1}{2}(RA + LL) = \frac{3}{2}(LA - V_W)$$

Lead augmented Vector Foot (aVF) 412 has the positive electrode on the left leg. The negative pole is a combination of the right arm electrode and the left arm electrode:

$$aVF = LL - \frac{1}{2}(RA + LA) = \frac{3}{2}(LL - V_W)$$

Together with leads I, II, and III, Augmented Limb Leads aVR, aVL, and aVF form the basis of the hexaxial reference system, which is used to calculate the heart's electrical axis in the frontal plane.

Figure 5:
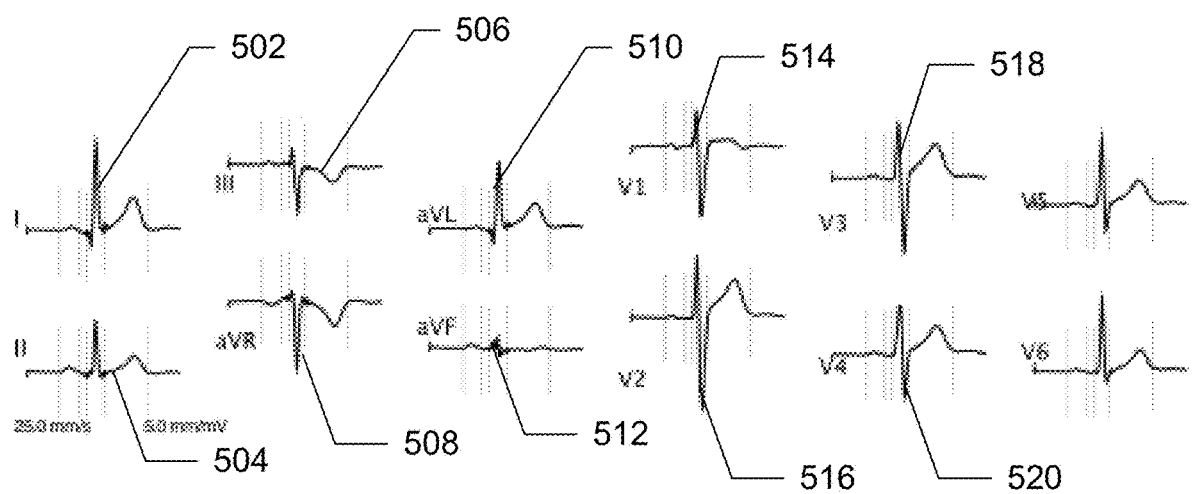
FIG. 5 is an exemplary diagram of an embodiment of signals detected on each of the leads.

The precordial leads lie in the transverse (horizontal) plane, perpendicular to the other six leads. The six precordial electrodes act as the positive poles for the six corresponding precordial leads: (V1, V2, V3, V4, V5 and V6). Exemplary signals detected on each of the leads are shown in FIG. 5. For example, a lead I signal 502, a lead II signal 504, a lead III signal 506, a lead aVR signal 508, a lead aVL signal 510, a lead aVF signal 512, a lead V1 signal 514, a lead V2 signal 516, a lead V3 signal 518, a lead V4 signal 520, a lead V5 signal 522, and a lead V6 signal 524 are shown. Wilson's central terminal is used as the negative pole.

In an embodiment, a networked electronic stethoscope may include two main functionalities. The first functionality may include enhanced stethoscope acquisition capabilities, and the second functionality may include linking the electronic stethoscope to a network of wireless sensors.

Figure 6:
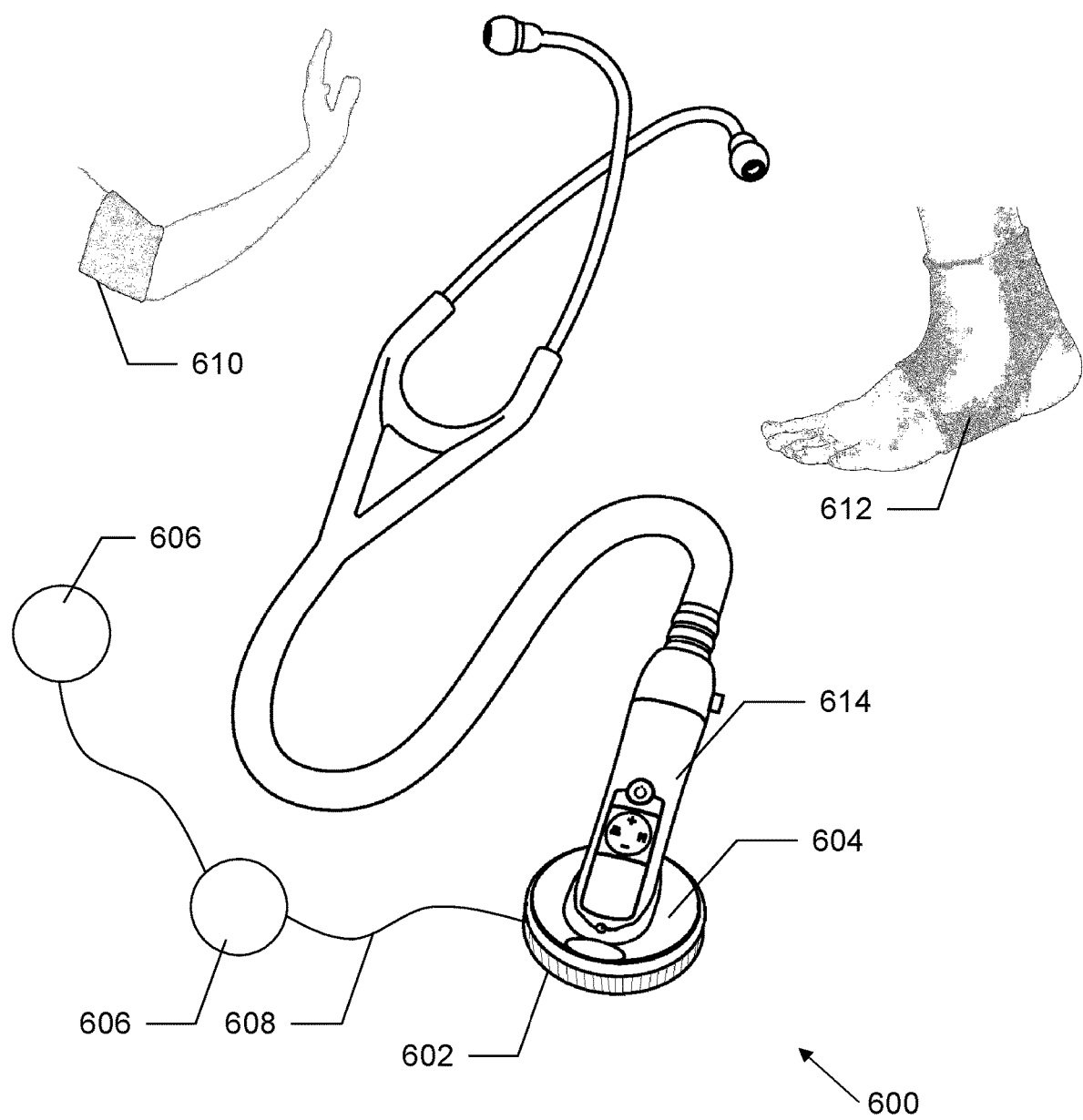
FIG. 6 is an exemplary diagram of an embodiment of a networked electronic stethoscope.

An example of an embodiment of a networked electronic stethoscope 600 is shown in FIG. 6. In this example, a networked electronic stethoscope may include a device 602 with a built-in electrode, a dedicated wireless network, such as Bluetooth, communication device 604, and a power supply 614. The device may be attached to a membrane support circle 604 of the electronic stethoscope 600. The device may be removable to allow a practitioner perform standard stethoscope assessment.

Equipped with this electrode setup, the stethoscope would enable the practitioner to easily measure cardiac related electrical signals from anywhere on the patient's body. The device may provide the capability to acquire physiological data related to all of the precordial leads. Indeed, these leads being located on the patient's torso, measuring them with a stethoscope-like device makes complete sense, as both the practitioner and the patient are used to such an examination type.

However, as corresponding data from limb leads must be acquired, additional electrodes 606 for limb lead signal acquisition may be needed.

In an embodiment a wire 608 may connect every sensor to a ground location as well as a wireless transmitter and an alimentation. However, this embodiment may cause discomfort to both the patient and the practitioner during the acquisition process.

In an embodiment, the electrodes 606 may be implemented as a tissue fabric armlet and/or anklet with built-in wireless (for example, Bluetooth) electrodes, driven by the stethoscope's controller. The electrode sensor technology may perform without any substantial lack of signal quality even when separated from the skin by layers of fabric. This would simplify the process of putting the electrodes on the patient. In addition, the discomfort caused by the electrodes/wire system would be reduced, allowing the patient to improved mobility.

In an embodiment, the system may include two or more armlet electrodes 610 and two or more anklet electrodes 612, driven by the stethoscope wireless network controller, that would stream continuously data from each of the limb leads and augmented limb leads to a computing device, such as a personal computer or smartphone, precordial leads signal acquisition is being performed with the stethoscope's built in electrode.

Figure 7:
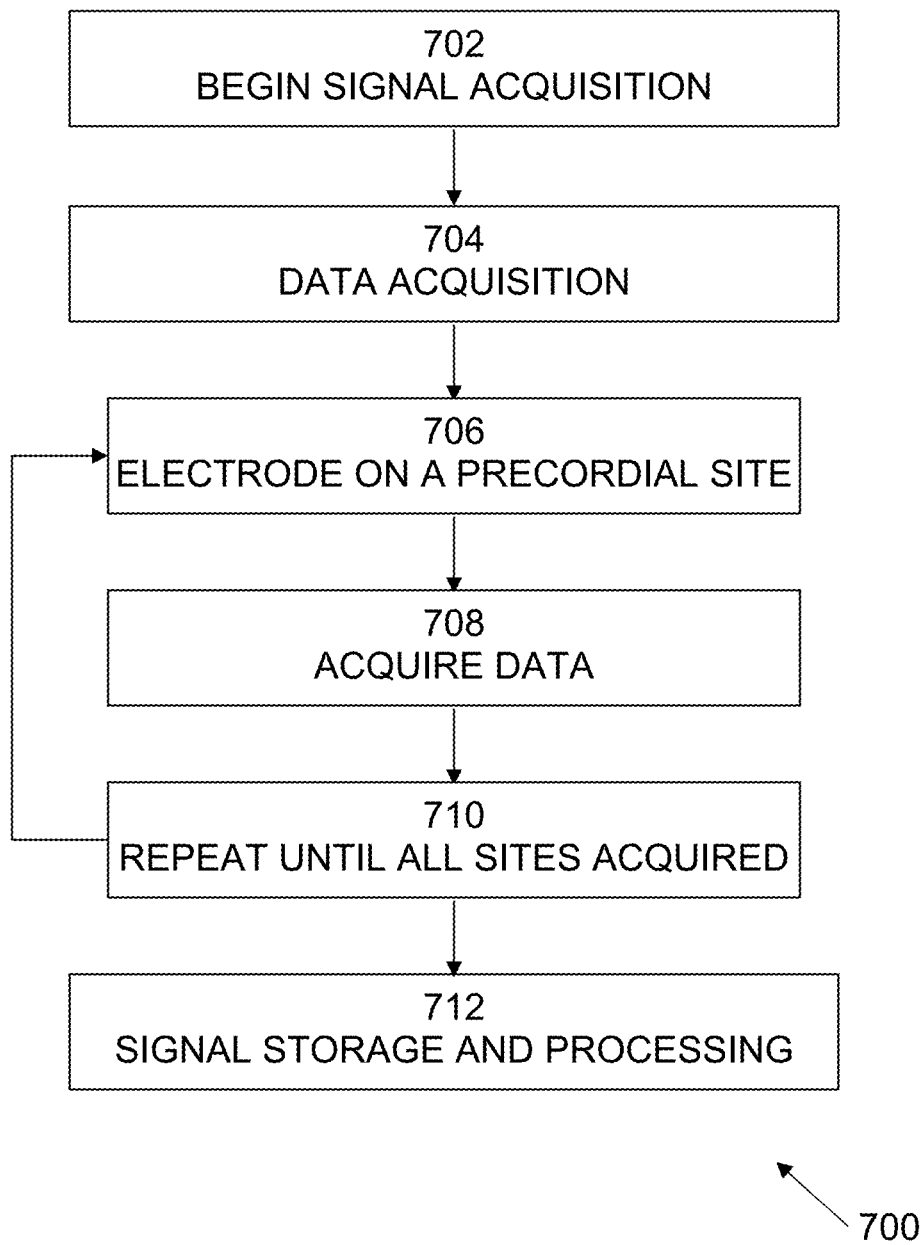
FIG. 7 is an exemplary flow diagram of an embodiment of a process for acquiring physiological data from a patient.

With the combination of both the armlet/anklet sensors and the electrode-enabled stethoscope, embodiments are capable of acquiring digitized 12 lead EKG data. An exemplary process 700 for acquiring such data is shown in FIG. 7. In the example shown in FIG. 7, data may be acquired continuously for the limb leads and augmented limb leads, while data may be acquired for only one or more precordial leads at a time. This may lead to a lack of synchronicity among the recorded precordial lead signals.

Process 700 begins with 702 the signal acquisition is begun utilizing the networked electronic stethoscope and the network thereof, such as a wireless network, such as Bluetooth. At 704, data acquisition is performed using the limb leads and augmented limb leads by attaching the armlet and anklet on the patient's limbs and beginning continuous data acquisition using those leads. At 706, a precordial lead electrode, for example, the electrode attached to the networked electronic stethoscope, is placed at a precordial site. At 708, data is acquired from the precordial site, as well as from the limb leads and augmented limb leads. Data may be acquired for a specific period, such as ten seconds. At 710, the process loops back to 706, where the precordial lead electrode, such as the electrode attached to the networked electronic stethoscope, is placed at another precordial site and the data acquisition is repeated for that precordial site. 706 and 708 may be repeated until data has been acquired for all precordial sites. At 712, the acquired data is stored and processed.

In this example, the physiological signals needed for a 12 lead EKG acquisition are acquired and processed. The results may be displayed on a computing device, such as a personal computer, smartphone, tablet, etc., and may be stored online for cloud-based applications, such as those described below.

Figure 8:
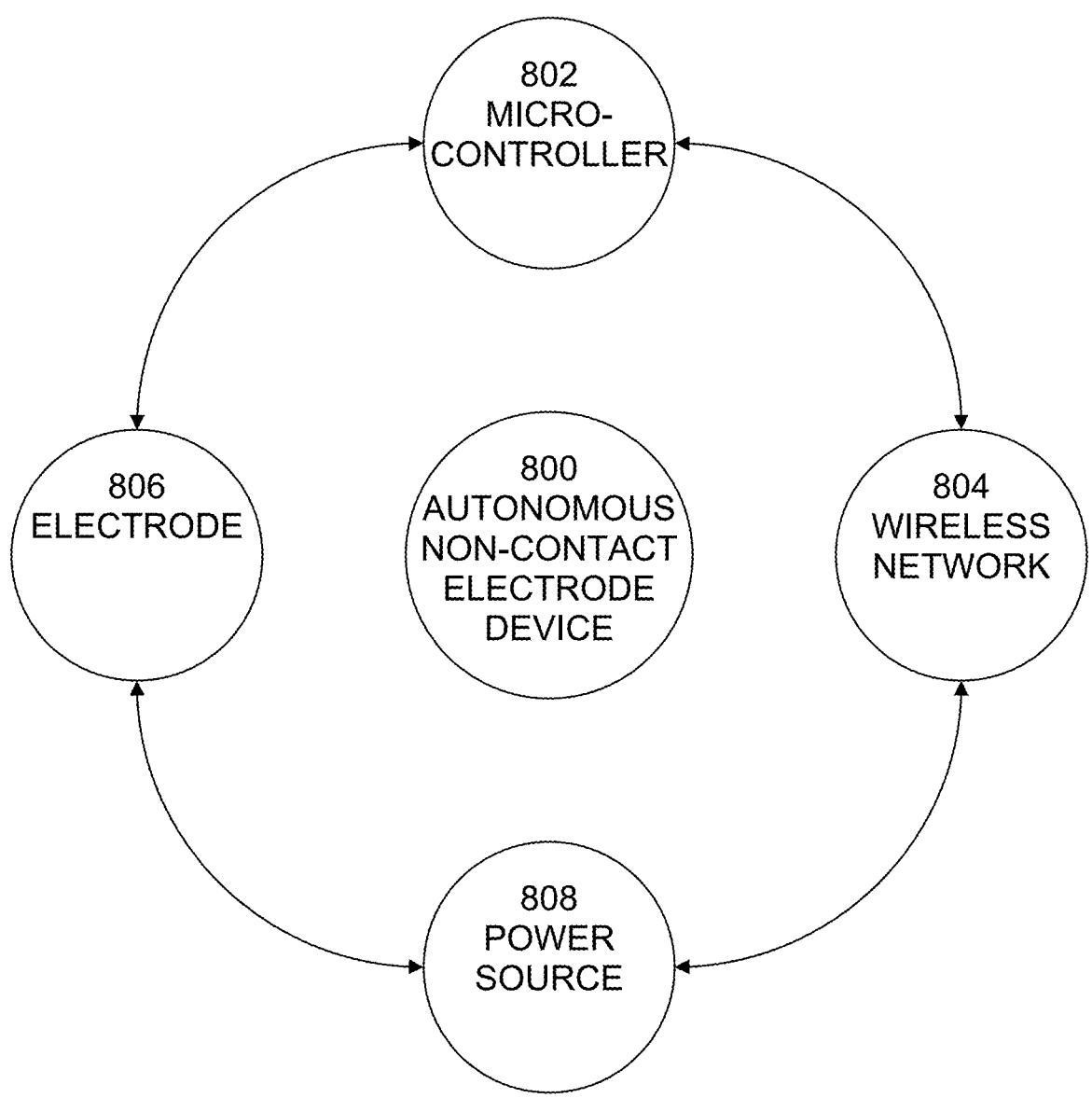
FIG. 8 is an exemplary diagram of an embodiment of a wireless sensor electrode device.

An exemplary embodiment of a wireless sensor electrode device 800 is shown in FIG. 8. Device 800 may include a micro-controller 802, a wireless network adapter 804, an electrode 806, and a power source 808. In this embodiment, each electrode device 800 may be autonomous. Each electrode device 800 may be attached to a tissue fabric armlet or anklet with built-in sensors, for placement on a patient. Micro-controller 802 may be, for example, a single-chip micro-controller, or an embedded processor in an FPGA or ASIC device. Wireless network adapter 804 may implement a standard wireless network protocol, such as Bluetooth, or it may implement a proprietary or custom wireless network protocol, or any other wireless network or communication protocol, and may be implemented as a separate device from the micro-controller device, or may be implemented in the same device, such as an FPGA or ASIC device, as the micro-controller device. Power source 808 may typically include a rechargeable or non-rechargeable battery and may further include power conditioning circuitry and battery charging circuitry. Such circuitry may be implemented as a separate device from the micro-controller and/or wireless network device, or may be implemented in the same device, such as an FPGA or ASIC device, as the micro-controller device and/or wireless network device.

Although conventional EKG systems typically utilize a wired ground electrode to provide a point of potential difference for signal measurement, embodiments may not require such a wired ground electrode. For example, as it is used to define potentials within an electrical circuit, EKG electrodes already measure potentials, which include the data needed to assess the patient physiological signals. Accordingly, in an embodiment, the desired EKG signals may be synthesized without any actual ground connection, using mathematical processing to build the EKG from the signals that are obtained from the electrodes. In an embodiment, as the signal from the electrodes is immediately digitized within the built-in electronic circuit, a ground connection may be stimulating by utilizing a digitized, transmitted equivalent of a ground signal. Such a signal may be used to directly rebuild EKG signals.

In an embodiment, the device may acquire four signals, from two armlets and two anklets, all driven by wireless network of the stethoscope. The device may then record and stream the data directly to the practitioner's smartphone, tablet or computer. As an example, three sensors, such as the left armlet, right armlet, and left anklet, may be used as sensors for data acquisition, whereas the remaining sensor, such as the right anklet, may be used as the artificial ground connection. Once all of those sensors are attached, the global acquisition process may be performed by a practitioner.

In an embodiment, the electrodes may be incorporated in armlets/anklets in a similar way, but utilizing a wire to connect each of them. Only one of the electrodes, such as the right leg anklet, may include the wireless network adapter and power unit, as well as a traditional ground reference. This embodiment may require the electrode of the stethoscope to be linked to the wire, which may limit the freedom of movement of both the practitioner and patient. In such an embodiment, the wire may be designed to provide improved comfort for each user.

In an embodiment, the storage of digitized biometric data may be provided on a number of devices, such as a smartphone, tablet or laptop, in addition to storage (and analysis) in the cloud or local server. This pooling of synchronous, multimodal data may create an opportunity for medical professionals to collaborate with one another and leverage Big Data computing, opening the door to additional innovative applications.

For example, in an embodiment, preliminary data processing capabilities may be provided on the devices and back-end analytic technology may be provided in the cloud or local server.

Figure 9:
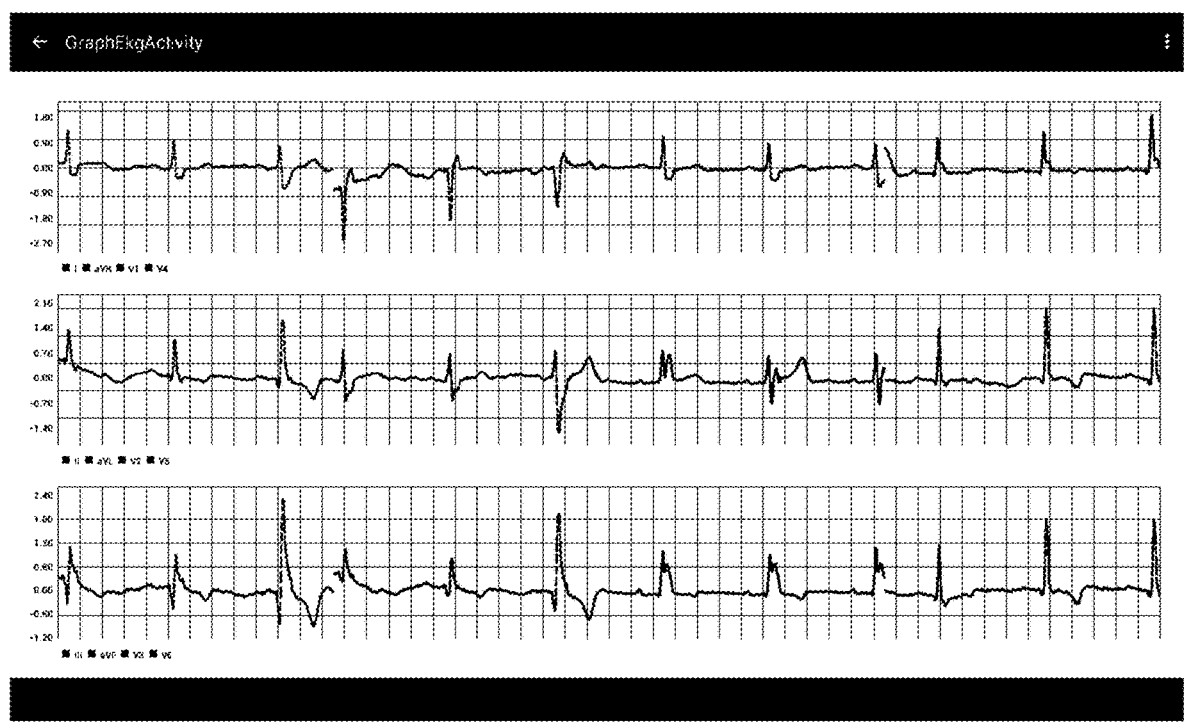
FIG. 9 is an exemplary diagram of an embodiment of an electro-cardiogram (EKG) display.

For example, in an embodiment, a software application for a computing device, such as a smartphone, tablet, computer, etc., may provide the capability for wireless stethoscope interfacing, collecting signals from a set of sensors, preliminary data processing, analyzing, and uploading on to the cloud or local server based platform. This application may provide a practitioner's window into the digitized physiological profile of his patient. An example of an EKG display 900 provided by such an application is shown in FIG. 9.

It is to be noted that the application is applicable not only to EKG display interfacing, but is also applicable to a variety of sensor devices capable of assessing diverse physiological signals from the patient. As such, the application may provide the capability to easily integrate new parts as new sensors are created. The application may provide an interface that is familiar and easy to use for the practitioner. The application may provide the capability to display many of the classical tools previously used by the practitioner. The application may provide the capability to perform advanced data processing both locally and in collaboration with the cloud platform or local server. The application may be responsive and efficient with computation time, whether it is for graph displaying, data crunching or dialog with the cloud platform or local server. The application may provide a first step to digitally assisted medicine and may connect to a massive, state of the art backend data analytics platform in the cloud.

Figure 10:
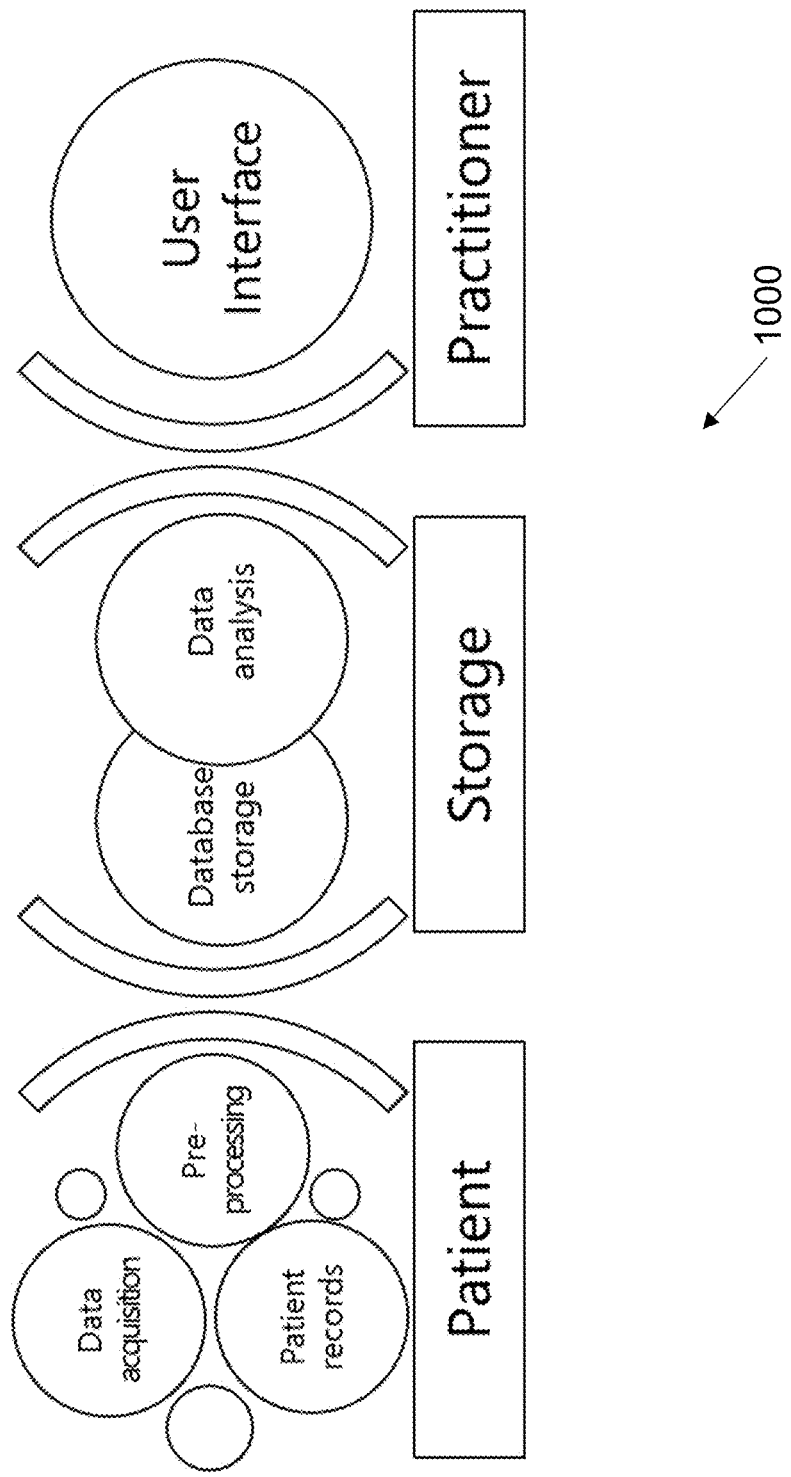
FIG. 10 is an exemplary diagram of an embodiment of a communication platform.

In an embodiment, a communication platform may provide the capability for various practitioners around the world to share and contribute to medical knowledge. An example of such a communication platform 1000 is shown in FIG. 10. Every practitioner has acquired through years of personal practice a specific, personal insight regarding medicine and diagnosis. As this experience makes a better doctor, it also engenders specialization and so one practitioner might lack efficiency when facing a patient that quite doesn't fit their mental map of diseases and diagnosis. Even though that specific doctor might be at a loss in a specific case, another with a different set of experience might be right in their comfort zone, and completely able to diagnose quickly, surely and securely. Such a communication platform may provide the capability to map a practitioner to a specific condition, with pooled former patient, treatment and outcome data. The communication platform may provide the capability to quantify patient data sufficiently to enable comparisons to be made. Indeed, with precise physiological data extracted from every patient, patterns may be found in both clinical data and clinicians themselves. Through ongoing analysis a doctors profiles may be defined from their past experiences, diagnoses and outcomes, thus allowing connection of two practitioners when needed.

In an embodiment, a number of processes may be performed by communication platform 1000, shown in FIG. 10. For example, communication platform 1000 may perform patient oriented processes, such as a practitioner performing a number of different examinations, all of which can be captured and uploaded by several means, such as text, binary item for simpler criteria, pictures or data obtained from hardware dedicated to acquire digitized physiological signals (such as our device). When the practitioner has enough information from the digitized data presented on the device, combined with his past experience to diagnose the patient. The practitioner may choose to get a second opinion from another doctor connected to the database. The platform chooses the best fit for the case the practitioner is dealing with. If both doctors accept the platform's proposal, the patient's data is shared to the second practitioner, who can share his insight to the first doctor.

Figure 11:
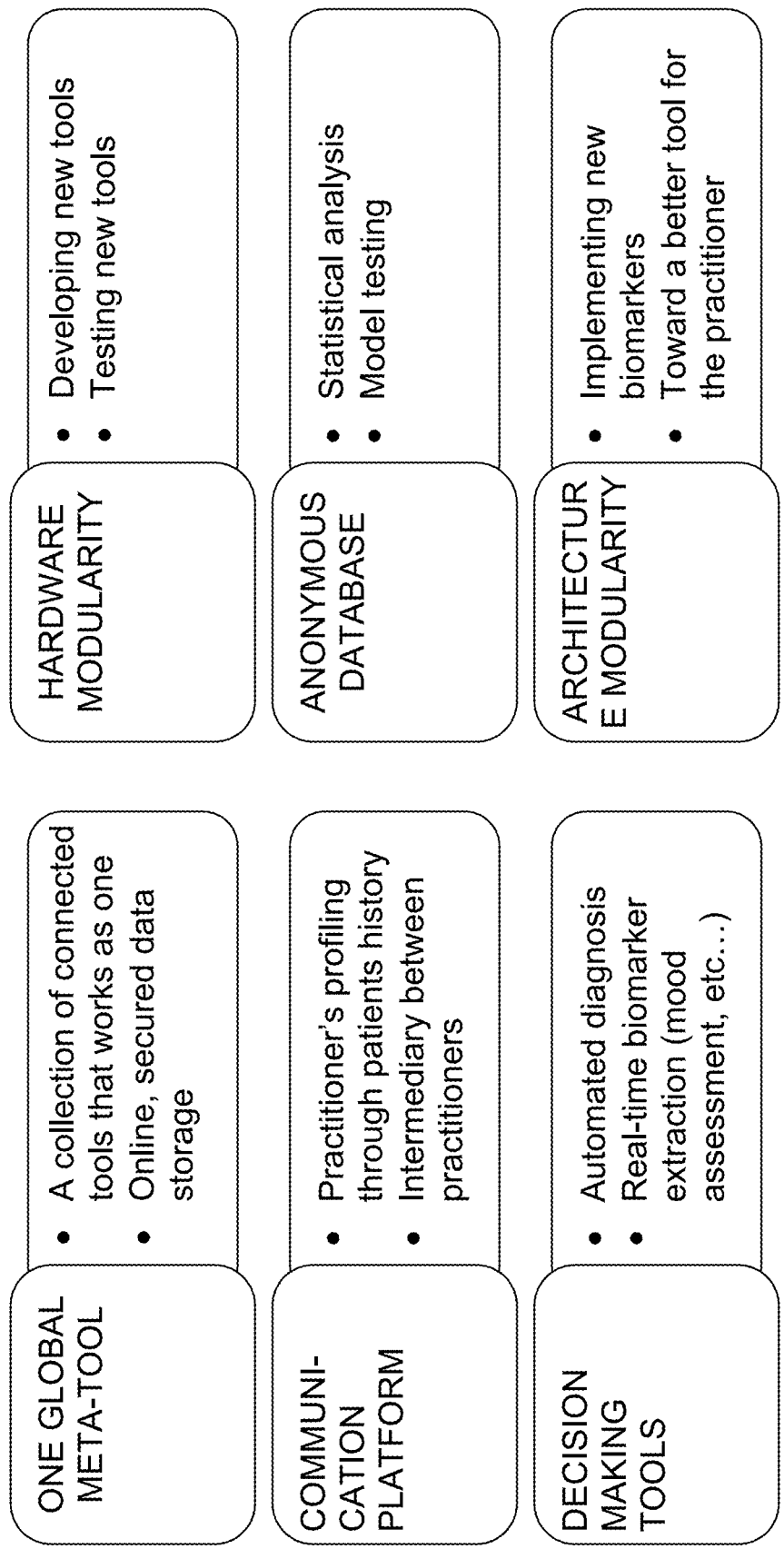
FIG. 11 is an exemplary diagram of advantages provided by an embodiment of a communication platform.

Such a communications platform may provide several advantages and functions, as shown in FIG. 11. First, it would give practitioners a tool with which they can transparently share their insights with the world, making every member doctor a member of a massive community-based diagnosis meta organism. In an embodiment, that machine learning could be applied to analyze these interactions to allow this "meta organism" to learn with each new patient treated. In the short term, expert assistance will allow practitioners to offer better diagnoses and over the longer term will capture these lessons learned to empower practitioners to learn from each other's experience. Secondly, although Big Data medical applications and decision support systems are generally intimidating to medical staff, this application is relatively non-invasive, meaning that all data and diagnosis-related decision remains in the hands of a human being that has demonstrated their ability in making such decisions. The transparent, non-invasive method of data collection and sharing presented by embodiments of this system is likely the best way to introduce the medical world to this Big Data revolution that is transforming so many other industries. Finally, this application is, from an algorithmic point of view, relatively easy to implement:

Each practitioner uses the hardware solution which uploads the patient's data online.

Using machine learning, clustering algorithms may classify patients by their similarities between their respective physiological signals.

Practitioners nay be classified from the types of patients they are most used to treating may be developed.

Practitioners with similar cases may get in touch with each other. For example, one practitioner might be specialized in one particular disease. While a naive approach may put every doctor confronted to such a disease in touch with said specialist (which would be overwhelming), a more sophisticated approach may utilize a network of information transmission and passive feedback to provide improved functionality.

Embodiments may provide practitioners a first glimpse of what Big Data assisted medicine could be, allowing them to get used to the implementation of data science tools in the diagnosis process.

Embodiments may provide is a massive tool allowing the implementation of automated diagnosis of several diseases from biomarker detection. Given the large amount of data collected by the system, the cloud platform has the potential to become one of the most massive sets of physiological signal data tied to case studies, treatments, outcomes and other medical related items. Indeed, each time a patient gets an examination, their data may be uploaded and (with patient consent) may contribute to the enrichment of the overall platform (in an anonymized, HIPAA-compliant way). This data may be accessible by any member of the community of practitioners contributing to the platform. As a consequence, each doctor may help to create a massive (as well as highly diverse) dataset that can provide one with information regarding a whole set of different diseases.

Such a dataset, in combination with powerful, specialized tools, such as the latest data analysis techniques, may provide any medical researcher with a significant insight. Over the longer term, such a system in combination with expert learning systems may allow the implementation of automated diagnosis algorithms.

Figure 12:
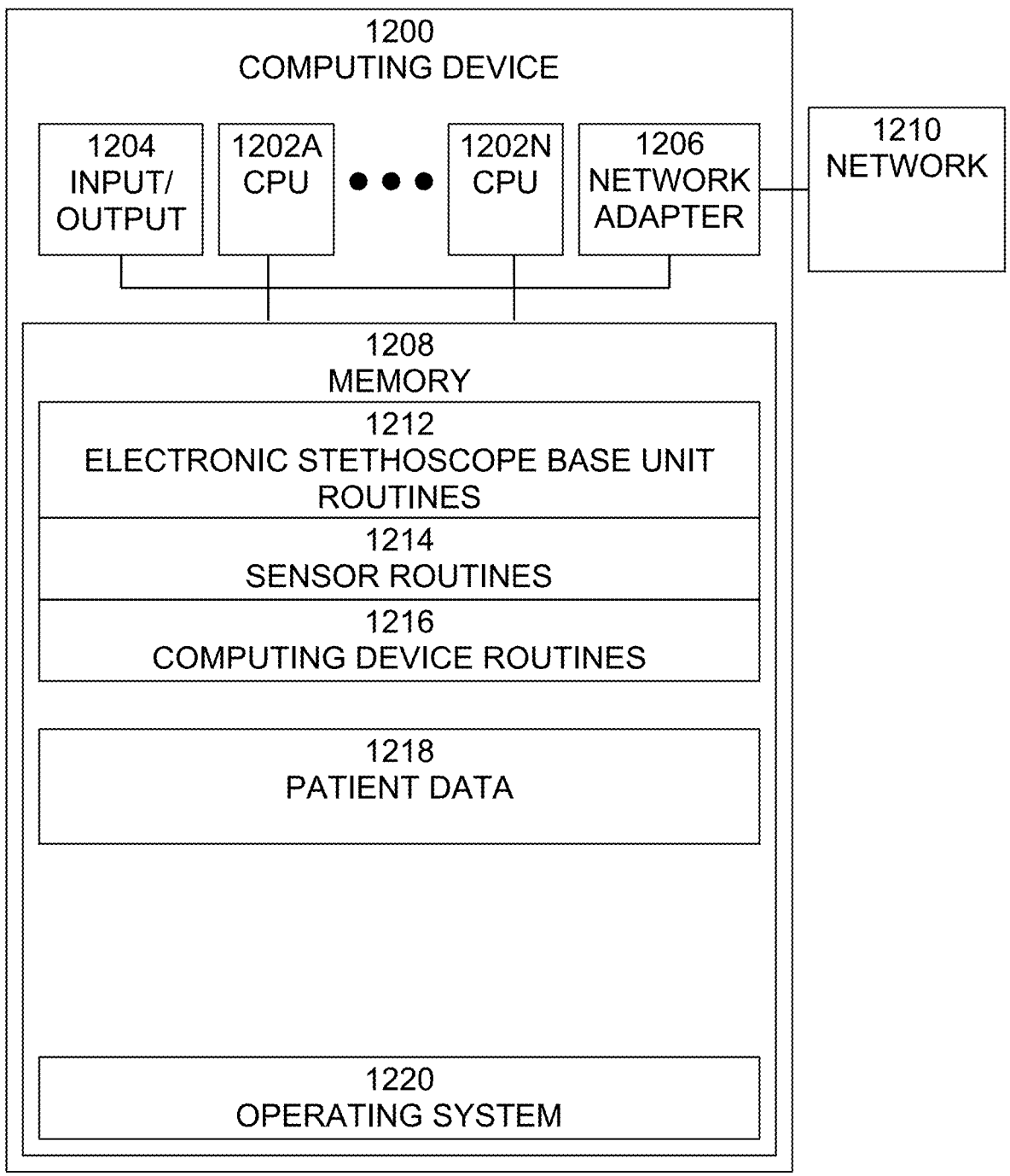
FIG. 12 is an exemplary diagram of an embodiment of a computing device, in which processes involved in the embodiments described herein may be implemented.

An exemplary block diagram of a computing device 1200, in which processes involved in the embodiments described herein may be implemented, such as those processes performed by an electronic stethoscope base unit 102, a sensor 108, 110, or a computing device 106, as shown in FIG. 1, is shown in FIG. 12. Computing device 1200 is typically a programmed general-purpose computer system, such as an embedded processor, system on a chip, personal computer, workstation, server system, and minicomputer or mainframe computer. Likewise, computing device 1200 may be implemented in a wrist-worn, or other personal or mobile device, and may include sensor circuitry as well as display circuitry to display object identification information. Computing device 1200 may include one or more processors (CPUs) 1202A-1202N, input/output circuitry 1204, network adapter 1206, and memory 1208. CPUs 1202A-1202N execute program instructions in order to carry out the functions of the present invention. Typically, CPUs 1202A-1202N are one or more microprocessors, such as an INTEL PENTIUM® processor. FIG. 12 illustrates an embodiment in which computing device 1200 is implemented as a single multi-processor computer system, in which multiple processors 1202A-1202N share system resources, such as memory 1208, input/output circuitry 1204, and network adapter 1206. However, the present invention also contemplates embodiments in which computing device 1200 is implemented as a plurality of networked computer systems, which may be single-processor computer systems, multi-processor computer systems, or a mix thereof.

Input/output circuitry 1204 provides the capability to input data to, or output data from, computing device 1200. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 1206 interfaces device 1200 with a network 1210. Network 1210 may be any public or proprietary LAN or WAN, including, but not limited to the Internet.

Memory 1208 stores program instructions that are executed by, and data that are used and processed by, CPU 1202 to perform the functions of computing device 1200. Memory 1208 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 1208 may vary depending upon the function that computing device 1200 is programmed to perform. In the example shown in FIG. 12, exemplary memory contents are shown representing routines and data for embodiments of the processes described above, such as those processes performed by an electronic stethoscope base unit 102, a sensor 108, 110, or a computing device 106 of FIG. 1. However, one of skill in the art would recognize that these routines, along with the memory contents related to those routines, may not be included on one system or device, but rather may be distributed among a plurality of systems or devices, based on well-known engineering considerations. The present invention contemplates any and all such arrangements.

In the example shown in FIG. 12, memory 1208 may include electronic stethoscope base unit routines 1212, sensor routines 1214, computing device routines 1216, patient data 1218, and operating system 1220. For example, electronic stethoscope base unit routines 1212 may include routines that operate electronic stethoscope base unit 102 and interact with a sensor 108, 110, or a computing device. Sensor routines 1214 may include routines to capture data with sensors 108, 110 and interact with electronic stethoscope base unit 102. Computing device routines 1216 may include routines to interact with electronic stethoscope base unit 102 and to analyze patient data 1218 received therefrom. Operating system 1220 provides overall system functionality.

As shown in FIG. 12, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system comprising:
   a networked electronic stethoscope;
   a first sensor adapted to be attached to the networked electronic stethoscope, the first sensor comprising:
   an electrode adapted to obtain an electro-cardiogram (EKG) signal of a patient,
   a processor adapted to digitize and process the obtained signal to form data, and
   a wireless network adapter adapted to transmit the data to the networked electronic stethoscope; and
   a plurality of fixed sensors adapted to be attached to limbs of the patient, each fixed sensor comprising an electrode adapted to obtain an EKG signal of the patient and each fixed sensor further adapted to transmit the EKG signal of the patient to a computing device;
   wherein the first sensor is adapted to be repeatedly placed at different precordial locations on the patient, and the computing device is adapted to combine the signals obtained from the first sensor at each different precordial location and the signals obtained from the plurality of fixed sensors to generate a 12 lead representation of the EKG signal of the patient, wherein at least some of the generated EKG signals are synthesized without a ground connection utilizing a digitized equivalent of a ground signal transmitted from at least one of the fixed sensors.

2. The system of claim 1, wherein at least one of the first sensor electrode and the fixed sensor electrodes is a non-contact electrode adapted to obtain a signal representing a EKG signal of the patient without direct contact with the patient.

3. The system of claim 2, wherein at least one fixed sensor is communicatively connected to the first sensor adapted to be attached to the networked electronic stethoscope.

4. The system of claim 3, wherein at least one fixed sensor is communicatively connected to the first sensor adapted to be attached to the networked electronic stethoscope via at least one wire.

5. The system of claim 3, wherein at least one fixed sensor is communicatively connected to the first sensor adapted to be attached to the networked electronic stethoscope via a wireless communication network.

6. The system of claim 1, wherein the first sensor is adapted to be attached to a membrane support circle of the networked electronic stethoscope.

7. The system of claim 6, further comprising: at least one additional sensor comprising an electrode adapted to obtain a signal representing a physiological parameter of the patient.

8. A method comprising:
   attaching to plurality of limbs on a patient a plurality of fixed sensors, each fixed sensor comprising an electrode adapted to obtain an electro-cardiogram (EKG) signal of the patient;
   repeatedly placing at different precordial locations on the patient a first sensor attached to a networked electronic stethoscope, the networked electronic stethoscope comprising an electrode adapted to obtain an EKG signal of a patient, a processor adapted to digitize and process the obtained signal to form data, and a wireless network adapter adapted to transmit the data to the networked electronic stethoscope;

for each different precordial location on the patient at which the first sensor is placed, obtaining an EKG signal of the patient; and combining the signals to obtained from the first sensor at each different precordial location and the signals obtained from the plurality of fixed sensors to generate a 12 lead representation of the EKG signal of the patient, wherein at least some of the generated EKG signals are synthesized without a ground connection utilizing a digitized equivalent of a ground signal transmitted from at least one of the fixed sensors.

9. The method of claim 8, wherein at least one of the first sensor electrode and the fixed sensor electrodes are non-contact electrodes adapted to obtain a signal representing a physiological parameter of the patient without direct contact with the patient.

10. The method of claim 9, wherein at least one fixed sensor is communicatively connected to the first sensor attached to the networked electronic stethoscope.

11. The method of claim 10, wherein at least one fixed sensor is communicatively connected to the first sensor attached to the networked electronic stethoscope via at least one wire.

12. The method of claim 10, wherein at least one fixed sensor is communicatively connected to the first sensor attached to the networked electronic stethoscope via a wireless communication network.

* * * * *